US006539809B1

(12) United States Patent
Weiss et al.

(10) Patent No.: US 6,539,809 B1
(45) Date of Patent: Apr. 1, 2003

(54) TEST APPARATUS FOR MEASURING STRESSES AND STRAINS

(75) Inventors: Walter W. Weiss, West Hempstead, NY (US); John L. Sullivan, Ft. Salonga, NY (US); Jeffrey J. Bott, Setauket, NY (US); Jacek A. Eubig, Floral Park, NY (US)

(73) Assignee: Testing Machines, Inc., Islandia, NY (US)

( * ) Notice: Subject to any disclaimer, the term of this patent is extended or adjusted under 35 U.S.C. 154(b) by 0 days.

(21) Appl. No.: 09/543,948

(22) Filed: Apr. 6, 2000

Related U.S. Application Data

(60) Provisional application No. 60/128,326, filed on Apr. 8, 1999.

(51) Int. Cl.[7] ................................................. G01N 3/10
(52) U.S. Cl. ....................................................... 73/825
(58) Field of Search .......................... 73/799, 810, 800, 73/808, 1.15, 862.42, 825, 817, 789, 772; 140/123.5

(56) References Cited

U.S. PATENT DOCUMENTS

| | | | |
|---|---|---|---|
| 3,969,930 A | * 7/1976 | Prevorsek et al. | 73/91 |
| 4,096,741 A | 6/1978 | Sternstein | |
| 4,292,835 A | * 10/1981 | Bickford | 73/1 B |
| 5,172,737 A | 12/1992 | Scruggs et al. | |
| 5,438,863 A | 8/1995 | Johnson | |
| 5,913,246 A | * 6/1999 | Simonelli et al. | 73/808 |

FOREIGN PATENT DOCUMENTS

| | | |
|---|---|---|
| DE | 213 059 | 8/1984 |
| JP | 60154837 | 8/1985 |
| JP | 62203043 | 9/1987 |
| JP | 05149851 | 6/1993 |
| JP | 08178814 | 7/1996 |
| JP | 10267811 | 10/1998 |
| JP | 11037913 | 2/1999 |

* cited by examiner

*Primary Examiner*—Harshad Patel
(74) *Attorney, Agent, or Firm*—Gerald E. Hespos; Anthony J. Casella

(57) ABSTRACT

A test apparatus is provided for measuring loads applied to an object and for measuring the deformation of the object in response to the loads. The test apparatus includes a stationary work head and a movable arm. The movable arm is selectively movable toward or away from the stationary work head. A load cell has a driven end mounted to the movable arm and a sensing end spaced from the movable arm. A movable work head is mounted to the sensing end and is configured for applying a load to a test object positioned between the stationary and movable work heads. A liner scale also is mounted to the sensing end of the load cell, and a linear encoder or read head is mounted in spaced relationship to the linear scale. The encoder reads deflection in the apparatus in view of loads applied during a test. A controller is provided for moving the movable work head in accordance with test parameters. The controller also receives output from the load cell and the read head, and uses that outputted information to develop stress-strain analytical data.

12 Claims, 4 Drawing Sheets

TEST APPARATUS FOR MEASURING STRESSES AND STRAINS

This application claims the benefit of U.S. Provisional Patent Appl. No. 60/128,326 filed Apr. 8, 1999.

BACKGROUND OF THE INVENTION

1. Field of the Invention

The subject invention relates to a test apparatus for performing stress and strain analysis on a test object.

2. Description of the Related Art

Engineers and manufacturers endeavor to make products that meet certain performance specifications, while minimizing costs. The size and shape of a product typically affect both the cost and performance of the product.

One way of measuring performance of a product is to assess how the product will perform in response to applied loads. Loads may be applied to a product at various stages through the life of the product, including, during manufacturing, during packaging or shipping and during usage. Data describing the reaction of a product to loads applied at various stages during the product life enable engineers to make more informed design decisions. However, collection of this data often is time consuming and costly. Furthermore test data for small test objects often is not sufficiently accurate or of high enough resolution to be useful.

The prior art includes test equipment that is capable of applying a specified load to a product for a specified duration. The product may be analyzed after the load has been terminated to assess the performance of the product in response to such a load. Tests of this type may be carried out during the prototyping stage of a product development to determine if further design changes may be warranted. Tests of this type also may be carried out on a samples of products from a manufacturing line to assess the ability of manufacturing equipment to produce products in accordance with the specifications. However, prior art machines of this type generally do not account for dimensional changes that may occur in the products in response to the applied load. More particularly, the application of a load to a product will cause some yielding in the product. Thus, the location on the product to which the load had been applied may not be in the exact location that had existed prior to the application of the load. Consequently, the actual load applied to the product may be less than the load specified by a particular test. Other test equipment may be designed to measure dimensional changes in a product in response to applied loads. However, most prior art test devices of this type are not sensitive to relative changes in the applied load that are due to the movement of the parts being measured. Furthermore, the position sensor on most prior art test machines is located on the drive shaft, while the load cell is at the end of an arm that is cantilevered from the drive shaft. Thus, the position sensor does not account for deflection in the cantilevered arm, in the load cell, or in the lead screw assembly.

Most prior art test machines are manufactured for a specific type of test. Thus, portions of the test apparatus that contact a product are substantially dedicated to the specific product being tested. Furthermore, a prior art test apparatus intended for compression analysis typically would not be suited for tensile analysis.

The inventors herein have recognized the need for reliable, rapid and accurate test data in a broad range of industrial and manufacturing environments. For example, test devices could be employed to analyze the forces required to mate two electrical connectors and to consider the yield of electrical contacts in response to various applied loads. In other instances, it may be desirable to assess the force required for puncturing the skin of a patient with a hypodermic needle. The dimensions and bevel angle of the needle may be varied to achieve an optimum puncture. In still other instances, forces and deflection may be analyzed to assess the various laminates of a blister package for tamper proof sealing of medicated capsules. In all of these instances, the loads are small and accuracy is important.

In view of the above, it is an object of the subject invention to provide a test apparatus that can perform a broad range of tests that involve applying loads and measuring applied loads and deflection with great precision.

It is a further object of the subject invention to provide a test apparatus that can perform several types of tests, including tests in compression and tests in tension.

SUMMARY OF THE INVENTION

The subject invention is directed to a test apparatus having a base. Any of several stationary work heads may be removably mounted to the base, with the particular stationary work head being selected in accordance with the type of test being carried out and the characteristics of the object on which the test is being performed. For example, a substantially planar stationary anvil may be provided for performing compression tests on a test object having a planar load bearing face. In other situations, the stationary work head may be a non-planar anvil for performing compression tests on an object having a complementary non-planar load bearing surface. In still other situations, the stationary work head may include means for gripping one end of a test object to be analyzed so that an opposed end of the object may be gripped and pulled away from the stationary work head.

The test apparatus of the subject invention further includes a support extending from the base. A drive means may be in or adjacent the support and may extend from the base. For example, the drive means may be a drive screw aligned perpendicular to the top surface of the base. A motor may be mounted in proximity to the base or the support and may be operative to drive the drive means, such as the drive screw.

A movable arm is mounted to the drive means and is selectively movable toward and away from the stationary work head. The movable arm includes an end with means for removably mounting a load cell.

A load cell assembly is mounted to the mounting means of the movable arm. In particular, the load cell assembly comprises a driven end and a sensing end. The driven end of the load cell assembly is removably mounted to the mounting means on the movable arm. The sensing end of the load cell assembly projects from the movable arm. The load cell accurately provides real time information that identifies magnitudes of loads applied by the movable arm. The load cell preferably is calibrated to a sensitivity of about 0.1 gram in compression, in tension or in both.

A movable work head or movable anvil is firmly mounted to the sensing end of the load cell assembly. The particular configuration of the movable work head or movable anvil is selected in accordance with the type of test being performed and in accordance with characteristics of the object on which the test will be performed. Thus, the movable work head may be a substantially planar anvil for performing compression tests on a product having a planar load bearing surface. Anvils of other shapes may be provided for performing compression tests on products that do not have a planar load bearing surface. Alternatively, gripping means may be provided for performing tensile tests.

The apparatus further includes a linear scale mounted to the sensing end of the load cell assembly. The linear scale preferably is parallel to the direction of movement of the movable arm. Thus the linear scale will move with the movable arm and the load cell toward and away from the stationary work head. A read head is fixed in slightly spaced relationship to the linear scale for sensing the magnitude of movement of the linear scale, the movable work head and the sensing end of the load cell relative to the stationary work head. The read head may be a linear encoder that is operative to read indicia on the linear scale precisely. The linear encoder preferably has a sensitivity for measuring dimensional movements of the drive arm of approximately 0.1 micron.

The test apparatus further includes a controller for controlling the operation of the carriage, the load cell and the linear scale. The controller may be operative to ensure that either force or displacement are applied in close agreement to a pre-defined function of each other or a predetermined function of time. For example, the controller may be operative to ensure that a constant load is maintained despite dimensional changes in the object being tested. Furthermore, the controller may be operative to ensure that precise measurements can be made of dimensional changes that are caused by the applied load. The controller may further be connected to a display means, such as a computer screen or a printer. The display means may be operative to tabulate the test results or to graphically present the test results. Thus, for example, the controller may provide real time stress-strain curves to show the way a product reacts to applied loads over time. The display means may be operative to receive input, and hence may be a touch sensitive screen.

DETAILED DESCRIPTION OF THE PREFERRED EMBODIMENT

Figure 1:
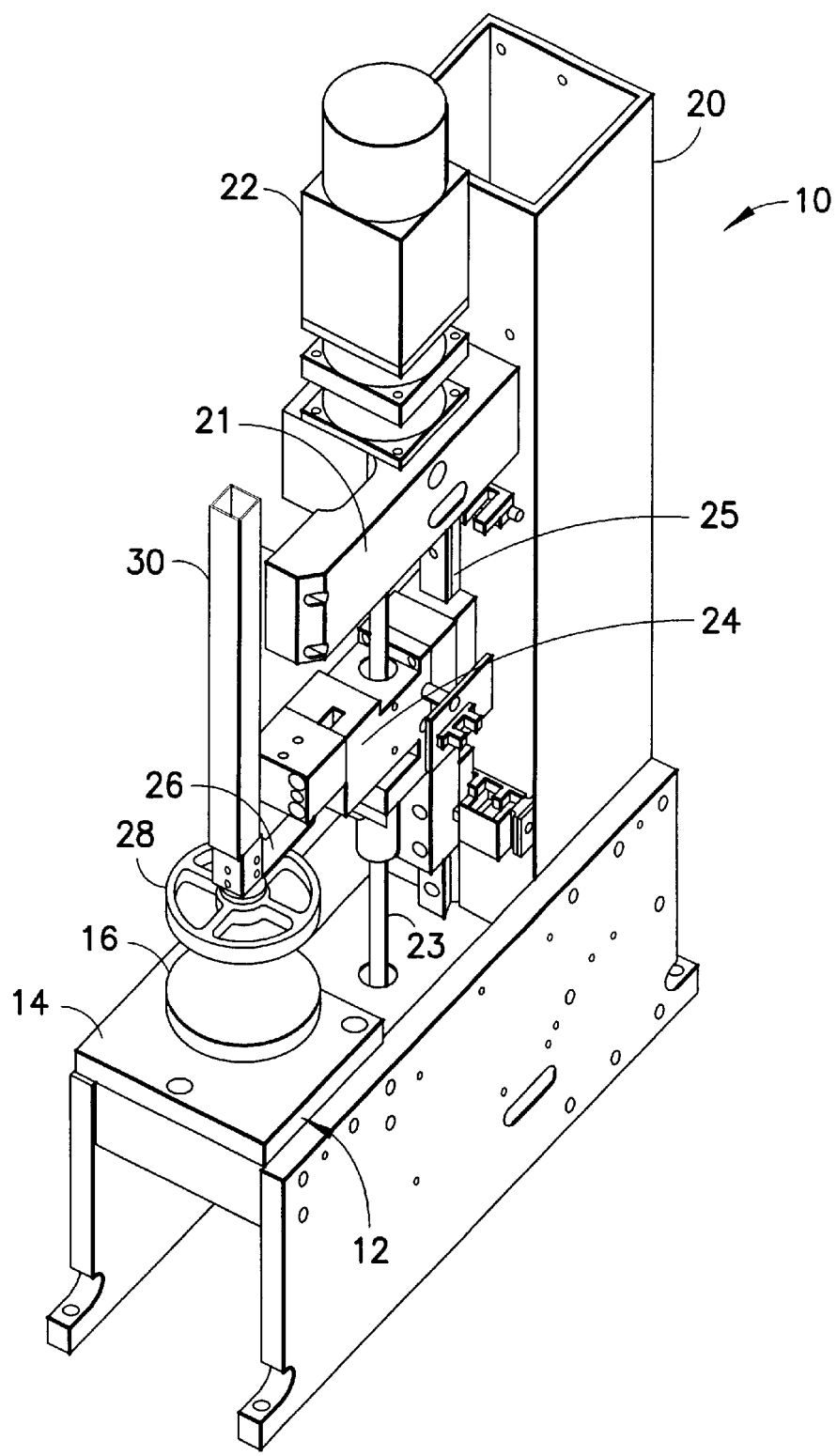
FIG. 1 is a perspective view of a test apparatus in accordance with the subject invention.
Figure 2:
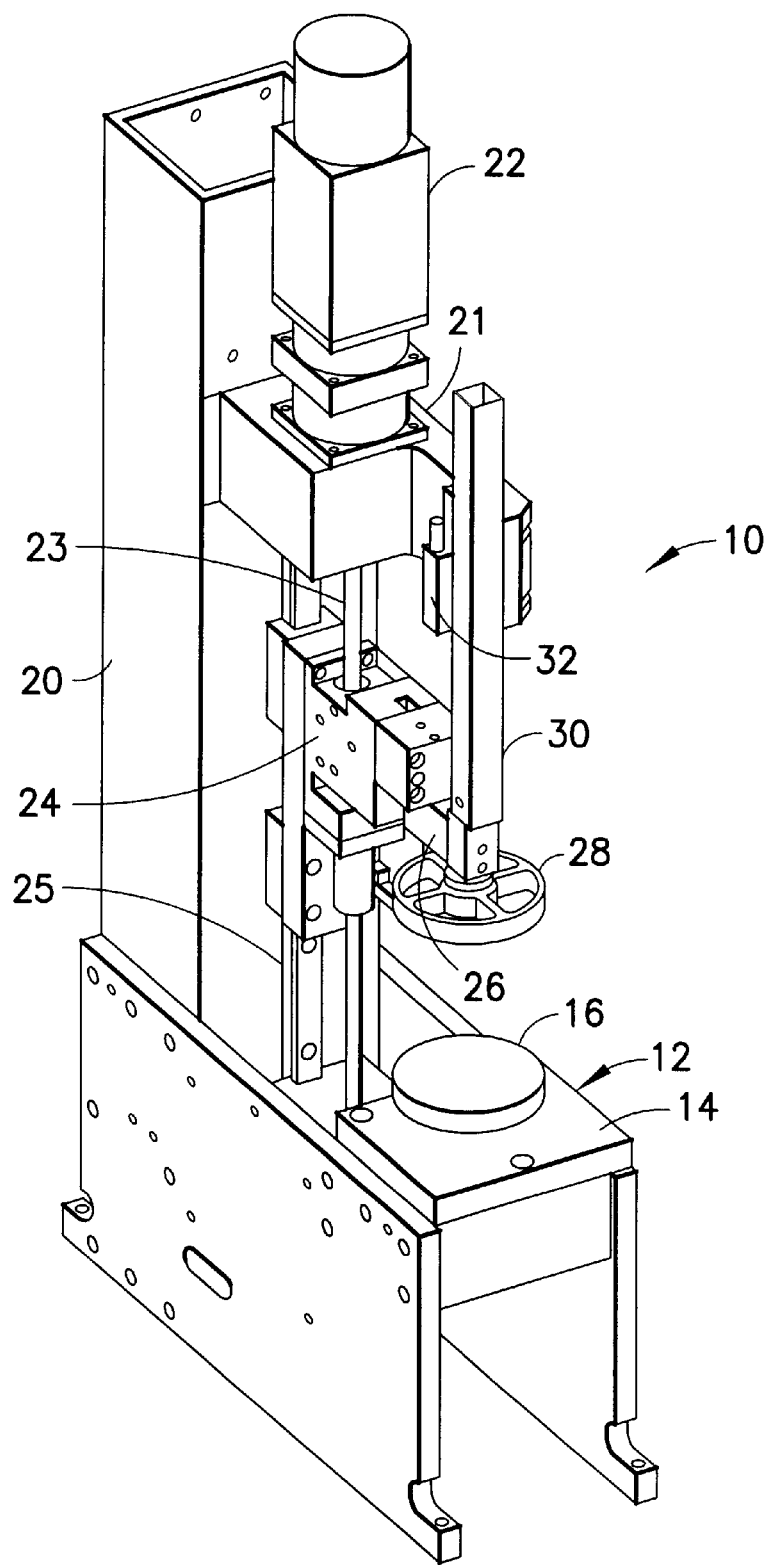
FIG. 2 is a second perspective view of the test apparatus.
Figure 3:
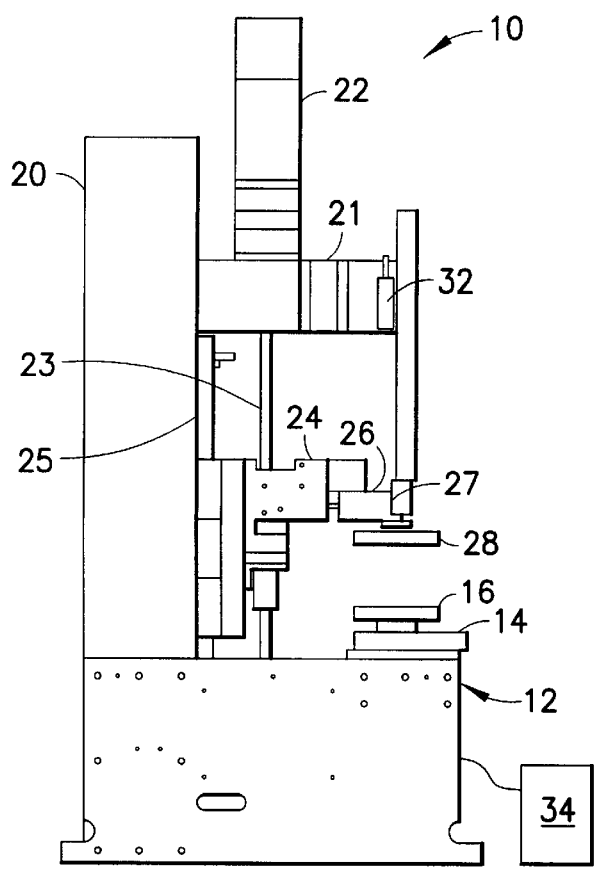
FIG. 3 is a side elevational view of the test apparatus as viewed from the left side of FIG. 1.
Figure 4:
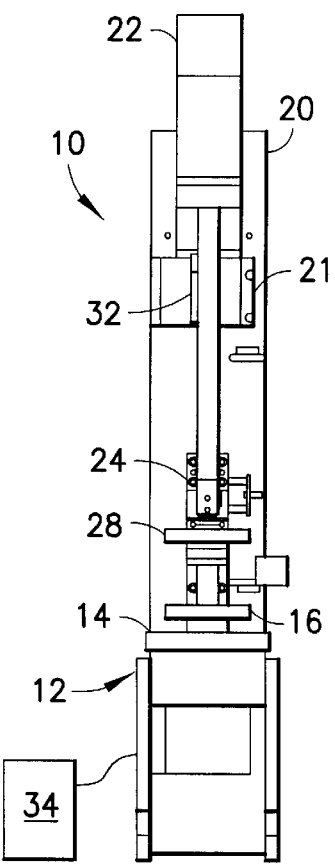
FIG. 4 is a front elevational view of the test apparatus.

A test apparatus in accordance with the subject invention is identified generally by the numeral 10 in FIGS. 1–4. The test apparatus 10 includes a base 12 having a substantially planar horizontal top surface 14 thereon. A stationary work head 16 is removably mounted to the top surface 14 of the base 12. The stationary work head 16 shown in FIGS. 1–3 is a planar anvil for performing compression tests on an object having a planar load bearing surface or a non-planar surface that will have a point load applied thereto. However, the planar stationary work load head 16 shown in FIGS. 1–3 may be removed and replaced with a different work head, such as a non-planar anvil or a gripping structure.

The apparatus further includes a support 20 extending upwardly from a location on the base 12 spaced from the stationary work head 16. The support 20 is connected rigidly to the base 12 to substantially prevent or minimize deflection in response to loads applied during a test. A bracket 21 is fixed to a location on the support 20 spaced from the base 12. A motor 22 is mounted to the support 20 and rotatable drives a lead screw 23 for driving the moving parts of the test apparatus 10, as explained further herein. The lead screw 23 is substantially perpendicular to the top surface 14 of the base 12. The motor 22 may be a stepper motor, or other motor for generating accurately controllable and measurable motion.

A movable arm 24 is mounted to a linear guide bearing system 25 which is mounted to the support 20 to be parallel to the lead screw 23 and stiff in all radial directions. The linear guide 25 is radially preloaded to prevent backlash in any radial direction. The movable arm 24 also is mounted to the lead screw 23. More particularly, a nut (not shown) is rigidly mounted in the movable arm 24 and is threadedly engaged with the lead screw 23. The nut and the lead screw 23 are pre-loaded axially to prevent backlash. Thus the movable arm 24 is movable in response to a rotation of the screw 23 generated by the motor 22. More particularly, the movable arm 24 is movable parallel to the screw 23 along an axis aligned substantially perpendicular to the planar horizontal top surface 14 of the base 12.

Figure 5:
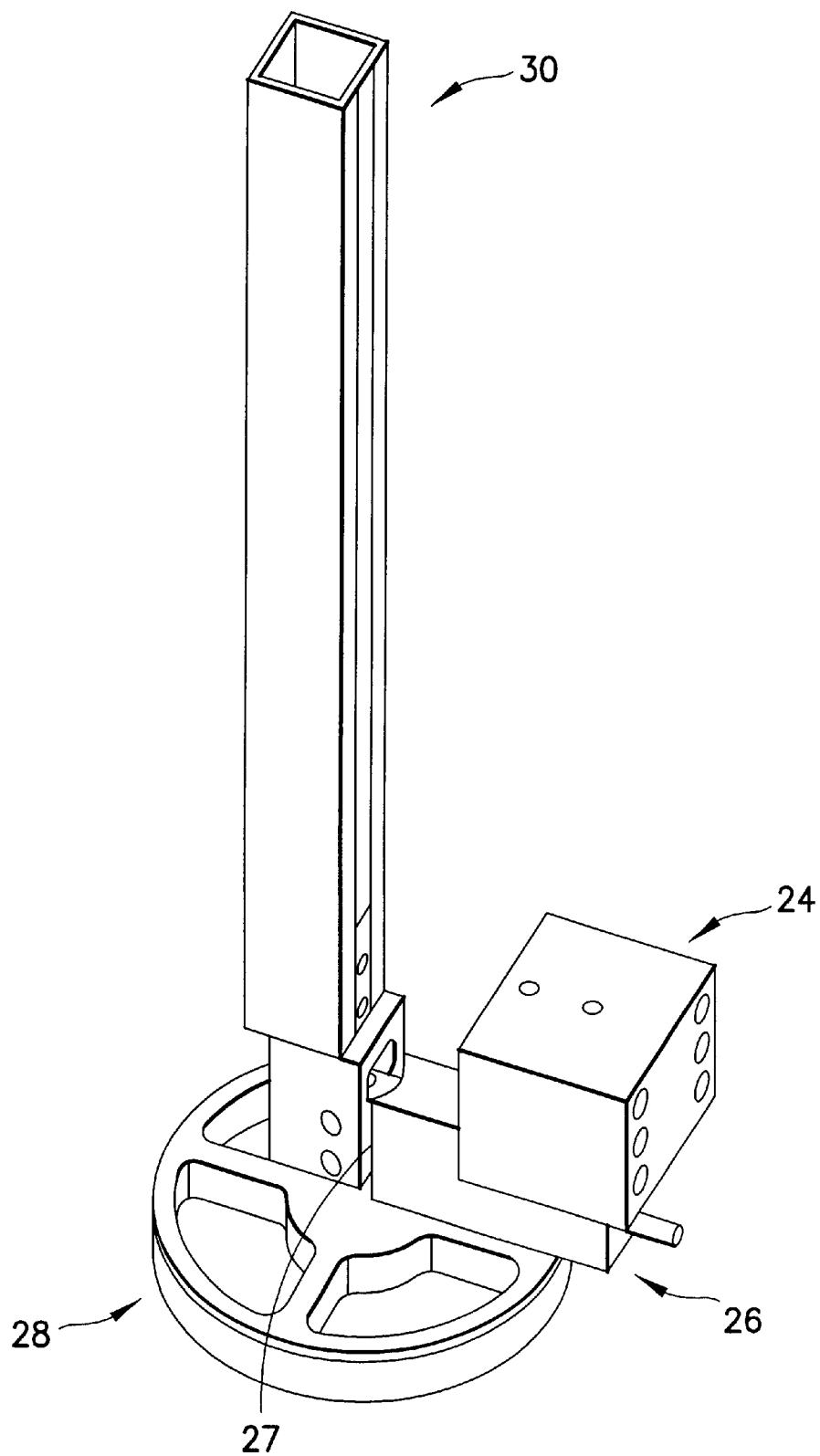
FIG. 5 is a perspective view of the movable arm, load cell, anvil and linear encoder.

A load cell assembly 26 has a base end or driven end mounted to an end of the movable arm 24 remote from the screw 23, as shown most clearly in FIG. 5. The load cell assembly 26 also has a sensing end 27 spaced from the movable arm 24. The load cell 26 is operative to precisely sense the magnitude of a load applied a test object. Preferably, the load cell 26 is sufficiently sensitive to measure loads in increments of 0.1 gram. The load cell preferably is operative to sense loads applied in compression or in tension depending upon the type of test being performed.

A movable work head 28 is removably mounted to the sensing end 27 of the load cell assembly 26. The movable work head 28 depicted in FIGS. 1–3 is a substantially planar anvil that is registered with the planar anvil defining the stationary work head 16. The planar anvil defining the movable work head 28 in FIGS. 1–3 would be appropriate for applying compression loads to an object having a planar load bearing surface, or for applying compressive point loads to an object having a non-planar load bearing surface, or to an object having a non-planar deformable surface. The planar anvil shown in FIGS. 1–3 can be removed and replaced with a non-planar anvil or with a gripping means that can perform tensile tests.

A linear scale 30 extends from the load cell 26 parallel to the screw 23, and substantially coaxially with the loads applied by the movable work head 28. Thus the linear scale 30 moves with the load cell 26, with the movable work head 28 and with the movable arm 24 along the axis of the applied force in response to operation of the motor 22. The linear scale 30 has measurement indicia extending along its length.

The apparatus 10 further includes a read head 32 mounted to the end of the bracket 21 remote from the support 20. The colinearity of the linear scale 30 and the applied load makes the deflection readings unaffected by varying orthogonality of the bracket 21. The read head 32 is a linear encoder that is operative to read encoded indicia on the linear scale 30 to an accuracy of approximately 0.1 micron of movement. The read head 32 does not contact the linear scale 30, and hence neither the read head 32 nor the load cell 26 are affected by friction or other forces generated in response to movement of the read head 32.

The apparatus 10 further includes a controller identified generally by the numeral 34 in FIG. 3. The controller 34 is operative to control the movement of the motor 22 in accordance with test parameters and is operative to receive output from the load cell 26 and the read head 32. The test parameters may ensure that force or displacement are applied in close agreement to a predefined function of each other or of time. The controller 34, for example, may be operative to provide input to the motor 22 to ensure that the movable arm 24 and the load cell 26 move for maintaining a constant pre-specified load on an object being tested, despite dimensional changes in the object. Alternatively, the controller 34 may be operative to provide input to the motor 22 to ensure that the movable arm 24 and the load cell 26 move for maintaining a specified dimensional change in the object being tested, and forces for achieving that dimensional change then may be outputted and analyzed. Still further, the controller 34 could operate the motor such that either forces or deflection vary in a pre-specified manner over time. The controller 34 communicates with a display apparatus 36. The controller may perform calculations on data from the load cell 26 and the read head 32 and may output information to the display 36. Thus, the display may produce real-time stress-strain graphs or other such displays for quantifying how an object responds to applied loads over time. The display 36 may produce information indicative of dimensional changes, as well as information regarding stresses produced by the applied load on the object. The display 36 also may provide input to the controller 34. For example, the display 36 may be a touch-sensitive screen.

The apparatus 10 provides a high degree of accuracy partly due to the positioning of the linear scale 30 on the sensing end 27 of the load cell 26, and substantially coaxially with the applied load. This provides much higher accuracy than systems that attempted to measure deflection with a rotary encoder located on the motor or lead screw, and eliminates errors that might otherwise be attributable to gear box backlash, hysteresis and lead error, lead screw coupler wind-up, lead screw bearing backlash and hysteresis, lead screw error, lead screw nut backlash deflection and hysteresis and load cell deflection. Thus, positional measurements are not affected by deflections in the movable arm 24, the load cell 26 or the screw 23 in response to the applied loads.

What is claimed is:

1. A test apparatus for applying test loads to a test object, said apparatus comprising:

an elongate support;

a stationary work head fixed in a spaced relationship relative to the elongate support for engaging a first location on the test object;

a movable arm having a mounting end mounted to the elongate support and a projecting end projecting from the movable arm, the mounting end being selectively movable relative to the elongate support along a direction of movement such that the projecting end of the movable arm is movable toward and away from the stationary work head;

a load cell having a driven end mounted to the movable arm and a sensing end;

a movable work head mounted to the sensing end of the load cell and being configured for applying a load to the test object in response to movement of the movable arm;

a linear scale mounted in fixed relationship to the load cell and aligned parallel to the direction of movement of the movable arm, said linear scale being substantially coaxial with the load applied to the test object; and a deflection reader mounted to the elongate support for measuring the position of the linear scale relative to the elongate support and the stationary work head, whereby the load cell measures loads applied to the test object, and whereby the deflection reader measures deflection of the movable arm during application of the test load to the test object.

2. The test apparatus of claim 1, wherein the deflection reader comprises a linear encoder.

3. The test apparatus of claim 2, wherein the linear encoder is operative to measure positional changes of the movable work head of approximately 0.1 micron.

4. The test apparatus of claim 1, wherein the load cell is operative to sense loads applied by the movable work head to the test object of approximately 0.1 gram.

5. The apparatus of claim 1, wherein the movable arm is linearly movable toward and away from the stationary work head.

6. The apparatus of claim 1, further comprising a controller for enabling and maintaining application of a selected load by the movable work head to the test object.

7. The apparatus of claim 1, wherein the fixed and movable work heads are substantially planar anvils disposed in substantially parallel relationship to one another.

8. The test apparatus of claim 1, further comprising means for moving the movable arm.

9. The test apparatus of claim 8, wherein the means for moving the movable arm comprises a lead screw, the linear scale being substantially parallel to the lead screw.

10. The test apparatus of claim 1, wherein the movable arm is between the deflection reader and the elongate support.

11. The test apparatus of claim 1, wherein the linear scale extends from the load cell in a direction away from the stationary work head.

12. The test apparatus of claim 1, wherein the deflection reader is spaced from the movable arm.

* * * * *